United States Patent
Kirk et al.

[11] Patent Number: 5,374,514
[45] Date of Patent: Dec. 20, 1994

[54] PHOTOTHERMOGRAPHIC MATERIALS

[76] Inventors: Mark P. Kirk, 8 Via 2nd Guigno, Carcare, Savona, Italy; Andrew W. Mott, 50 Portland Road, Bishops Stortford, Hertford, United Kingdom

[21] Appl. No.: 168,994

[22] Filed: Dec. 17, 1993

[30] Foreign Application Priority Data

Jan. 6, 1993 [GB] United Kingdom ............. 9300147

[51] Int. Cl.⁵ ............................................. G03C 1/498
[52] U.S. Cl. ........................................ 430/619; 430/600; 430/607; 430/613; 430/617
[58] Field of Search ............... 430/619, 617, 600, 607, 430/613

[56] References Cited

U.S. PATENT DOCUMENTS

| | | | |
|---|---|---|---|
| 3,874,946 | 4/1975 | Costa et al. | 430/617 |
| 3,877,940 | 4/1975 | Ericson | 430/617 |
| 4,108,665 | 8/1978 | Gutman et al. | 430/617 |
| 4,546,075 | 10/1985 | Kitaguchi et al. | 430/617 |
| 4,756,999 | 7/1983 | Swain et al. | 430/619 |
| 5,028,523 | 7/1991 | Skoug | 430/617 |
| 5,064,744 | 11/1991 | Fukui et al. | 430/617 |

*Primary Examiner*—Thorl Chea
*Attorney, Agent, or Firm*—Gary L. Griswold; Walter N. Kirn; Mark A. Litman

[57] ABSTRACT

A photothermographic material comprising photographic silver halide, a reducible silver source, a reducing agent for silver ion and a binder, and as an antifoggant and/or stabilizer, a compound of the formula (I):

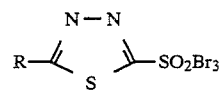

wherein R is a member selected form the group consisting of a hydrogen atom, an alkyl group, an aryl group and a heterocyclic group.

14 Claims, No Drawings

PHOTOTHERMOGRAPHIC MATERIALS

FIELD OF THE INVENTION

This invention relates to photothermographic materials and in particular to stabilisers and antifoggants for use therein.

BACKGROUND OF THE INVENTION

Heat-developable photosensitive materials which can produce photographic images using a dry heat processing method (referred to herein as "photothermographic materials") are known and described for example, in U.S. Pat. Nos. 3,152,904 and 3,457,075 and in "Thermally Processed Silver Systems" by D. Morgan and B. Shely, "Imaging Processes and Materials", Neblettes's Eighth edition; Edited by J. M. Sturge, V. Walworth and A. Shepp, p.2 (1969). Such photothermographic materials have a photosensitive medium comprising a reducible silver source, e.g. an organic silver salt; a catalytic amount of photocatalyst, e.g., silver halide, in reactive association with the reducible silver source, and a reducing agent for silver ion, ordinarily dispersed in an (organic) binder matrix. Although stable at ambient temperatures, when heated to higher temperatures, e.g., 80° C., or higher, after imagewise exposure, silver is produced in the exposed regions of the medium via a redox reaction between the reducible silver source and the reducing agent. This redox reaction is accelerated by the catalytic action of the exposure-generated silver catalyst. The silver provides a black image which contrasts with the unexposed areas, resulting in the formation of an image.

In practice, it is essential to include an effective antifoggant in such photothermographic materials, since without an antifoggant, some generation of silver in the unexposed areas takes place upon thermal development, resulting in a poor differential between image and background fog. In addition, one of the problems of photothermographic materials involves their post-processing stability. Since the process is performed without a fixing step, it is desirable to provide a means to enable room light handling of the final image.

Polybrominated organic compounds have been described as both antifoggants and image-stabilisers for photothermographic materials since they can oxidise reduced silver (fog) back to silver bromide under thermal (anti-foggant) and light exposed (image stabiliser) conditions.

Examples of such compounds are described in U.S. Pat. Nos. 4,546,075, 4,452,885 (tribromomethylheterocycles as anti-foggants), 3,874,946 (tribromomethylsulphonylaromatics as image stabilisers) and British Patent Application No. 9221383.4 (tribromomethylketones).

Due to the thermal processing of the photothermographic imaging material, all the compounds used in the construction of the material will be present in the final image sheet. All the materials included in such a material must be acceptable both environmentally and in their possible effect on those persons who might come into contact with the material. The materials must be determined to be non-mutagenic and also it is highly desirable that they do not sensitise the skin of those who come in contact with them. Many polybrominated organic compounds are known to be powerful skin irritants and sensitisers and it is desirable to find compounds having effective anti-foggant and image stability properties for photothermographic materials which exhibit acceptably low sensitisation to human skin.

BRIEF SUMMARY OF THE INVENTION

According to the present invention there is provided a compound of the formula:

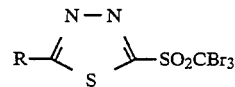

in which;

R represents a hydrogen atom, an alkyl group, an aryl group or a heterocyclic group, any of which groups may be substituted.

This small class of compounds are effective anti-foggants and image stabilizers in photothermographic materials and exhibit low skin sensitisation. The latter property is particularly surprising since other compounds of similar structure have proved positive in skin sensitisation tests.

DESCRIPTION OF PREFERRED EMBODIMENTS

Referring to formula (I), the group R is generally selected from hydrogen, alkyl groups comprising up to 10 carbon atoms, preferably up to 5 carbon atoms; aryl groups comprising up to 14 carbon atoms, preferably up to 10 carbon atoms; 5, 6, 7 or 8-membered heterocyclic ring nuclei and heterocyclic fused ring nuclei comprising up to 14 ring atoms, each of which groups, ring and fused ring nuclei may possess one or more substituents selected from alkyl groups (e.g., methyl, ethyl, isopropyl etc.), halogen atoms (e.g., fluorine, chlorine, bromine and iodine), a hydroxy group, alkoxy groups (e.g., methoxy, ethoxy etc.), aryloxy groups (e.g., phenoxy, hydroxyphenoxy etc.), amino groups (e.g., amino, methylamino, dimethylamino etc.), a cyano group, acylamino groups (e.g., acetylamino, benzoylamino etc.), diacylamino groups (e.g., succinimido etc.), ureido groups (e.g., methylureido etc.), sulphonamido groups (e.g., methylsulphonamido etc.), acyloxy groups (e.g., acetyloxy etc.), sulphamoyl groups (e.g., N-ethylsulphamoyl etc.), alkycarbonyl groups, arylcarbonyl groups, alkoxycarbonyl groups (e.g., methoxycarbonyl, ethoxycarbonyl etc.), aryloxycarbonyl groups (e.g., phenoxycarbonyl etc.), alkoxycarbonyl amino groups (e.g., ethoxycarbonylamino etc.), aryl groups (e.g., phenyl, tolyl etc.), hydroxyalkyl groups (e.g., hydroxyethyl, hydroxypropyl etc.), alkoxyalkyl groups (e.g., methoxyethyl, methoxypropyl etc.), mercapto groups, alkylthio groups, arylthio groups, alkylsulphonyl groups, arylsulphonyl groups, acyl groups, aralkyl groups, alkyl groups containing a carboxyl group (e.g., carboxymethyl, carboxyethyl etc.), each of which groups may where appropriate comprise up to 14 carbon atoms, preferably not more than 10 carbon atoms.

Examples of ring and fused ring nuclei represented by R include: isoxazole, pyrimidine, quinoxaline, indolenine and tetraazindene.

Examples of alkyl groups represented by R include: methyl, ethyl, propyl, isopropyl, butyl, isobutyl, t-butyl, pentyl, isopentyl, hexyl, octyl etc.

Examples of aryl groups represented by R include: phenyl, ethoxyphenyl, tolyl, xylyl, naphthyl etc.

As is well understood in this technical area, a large degree of substitution is not only tolerated, but is often advisable. As a means of simplifying the discussion, the terms "nucleus", "group" and "moiety" are used to differentiate between chemical species that allow for substitution or which may be substituted and those which do not or may not be so substituted. For example, the phrase "alkyl group" is intended to include not only pure hydrocarbon alkyl chains, such as methyl, ethyl, octyl, cyclohexyl, iso-octyl, t-butyl and the like, but also alkyl chains bearing conventional substituents known in the art, such as hydroxyl, alkoxy, phenyl, halogen (F, Cl Br and I), cyano, nitro, amino etc. The term "nucleus" is likewise considered to allow for substitution. Thus, the phrase "pyrimidine nucleus" would be understood to include not only an unsubstituted pyrimidine ring, but also pyrimidine rings bearing conventional substituents known in the art. The phrase "alkyl moiety" on the other hand is limited to the inclusion of only pure hydrocarbon alkyl chains, such as methyl, ethyl, propyl, cyclohexyl, iso-octyl, t-butyl etc.

conventional silver halide phothothermographic chemistry is used in the materials of the invention. Such chemistry is described in, e.g., U.S. Pat. Nos. 3,457,075, 3,839,049, 3,985,565, 4,022,617 and 4,460,681. Any of the various photothermographic media, such as full soaps, partial soaps, and the like may be used in the practice of the present invention, including both black-and-white and colour chemistries and either in situ halidised (e.g., as disclosed in U.S. Pat. No. 3,457,075) or preformed silver halide sources (e.g., as disclosed in U.S. Pat. No. 3,839,049) may be used.

Conventional photothermographic chemistry comprises a photosensitive silver halide catalyst, a silver compound capable of being reduced to form a metallic silver image (e.g., silver salts, both organic and inorganic, and silver complexes, usually light-insensitive silver materials), a developing agent for silver ion (a mild reducing agent for silver ion) and a binder.

The photothermographic chemistry may be black and white or colour-forming. In the latter type of material, the reducing agent generates a colour on oxidation, either by becoming coloured itself, or by releasing a dye during the process of oxidation. Any leuco dye capable of being oxidized by silver ion to form a visible dye is useful in the practice of the present invention. Dye-forming developers such as those disclosed in U.S. Pat. Nos. 3,445,234, 4,021,240, 4,022,617, 4,368,247 and 4,460,681 are useful, and also those disclosed in Japanese Patent Publication No. 82-500352, and likewise dye-releasing developers, such as those disclosed in U.S. Pat. No. 4,981,775.

The compounds of the invention may be incorporated into the photothermographic medium in the same manner as antifoggants of the prior art. The optimum concentration for individual compounds of the invention may vary widely. In some cases, starting from the minimum amount required to suppress fog, increasing the amount of the tribromomethyl sulphone compound leads to a loss of image density, but in other cases it may produce an increase in image density before levelling out. In general, the compounds of the invention are utilised in amounts of from about $1 \times 10^{-3}$ to about $1 \times 10^{-1}$ moles per mole of silver, although amounts outside this range may also be useful.

In addition to the compounds of the invention, the photothermographic media of the invention may also contain, as a speed enhancing agent, a heterocyclic ring compound of the type disclosed in U.S. Pat. No. 5,028,523 in which a nitrogen atom of the ring is electrically balanced by hydrobromic acid and which is associated with a pair of bromine atoms. The central nucleus of the nitrogen-containing heterocyclic compound may be generally represented by any of the following formulae:

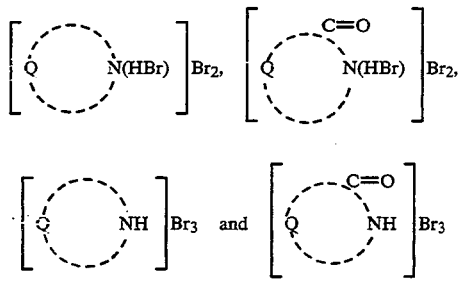

in which;

Q represents the atoms (preferably selected from C, S, N, Se and O more preferably C, N and O) necessary to complete a 5, 6, or 7-membered heterocyclic ring (monocyclic) or fused ring nucleus (polycyclic, especially bicyclic, with a fused-on benzene ring). The heterocyclic nucleus may possess one or more substituents selected from those defined for groups represented by R. Exemplary and preferred heterocyclic ring groups include pyridine, pyrrolidone and pyrrolidinone. Other useful heterocyclic ring nuclei include pyrocyclic rings, e.g., pyrrolidines, phthalazinone, phthalazine etc.

Preferred heterocyclic nuclei for use in the practice of the present invention may be defined by the formulae:

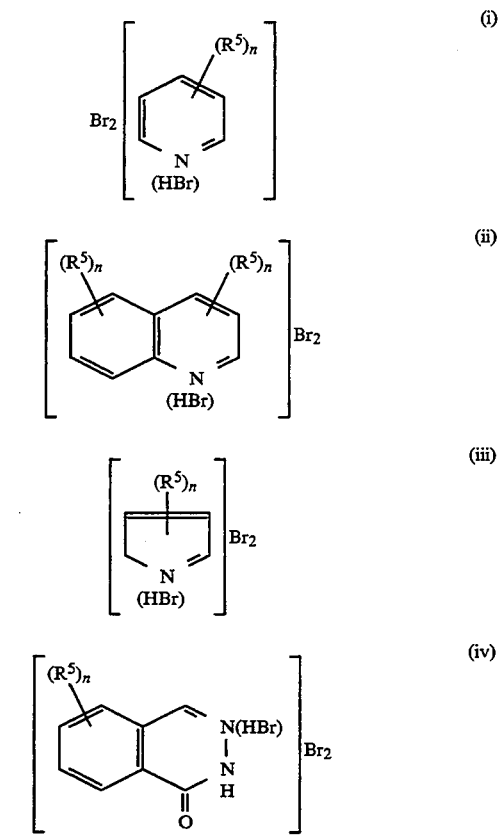

-continued

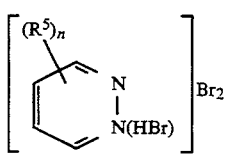

(v)

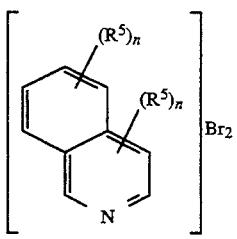

(vi)

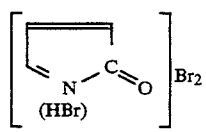

(vii)

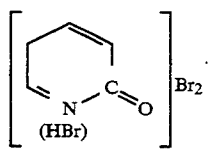

(viii)

in which;

n is 0 (zero) or has integral values of from 1 to 4, and each $R^5$ represents a substituent selected from those defined for groups represented by R, e.g., alkyl groups, alkoxy groups, aryl groups, nitro, cyano, and the like. Substituents on adjacent positions may form fused ring groups so that formula (i) above would in fact be inclusive of formulae (ii) and (iv).

These compounds are generally used in an amount of at least 0.005 moles/mole of silver. Usually the range is from 0.005 to 1.0 moles of the compound per mole of silver and preferably between 0.01 and 0.3 moles per mole of silver. The preferred level is currently about 0.01 moles/mole silver.

The preferred nitrogen-containing heterocyclic compound is pyridinium hydrobromide perbromide (PHP).

Photothermographic materials are usually constructed as one or two imaging layers on a substrate. Single layer constructions must contain the reducible silver source, the silver halide and the developer, as well as optional additional materials, such as toners, coating aids and other adjuvants. Two-layer constructions must contain the reducible silver source and silver halide in one layer (usually the layer adjacent the substrate) and the other ingredients in the second layer or both layers.

The silver halide may be any photosensitive silver halide, such as silver chloride, silver bromide, silver iodide, silver chlorobromide, silver bromoiodide, silver chlorobromoiodide etc., and may be added to the imaging layer in any fashion which places it in catalytic proximity to the reducible silver source. The silver halide generally comprises from 0.75 to 15% by weight of the imaging layer, although larger amounts of up to about 25% by weight, are also useful. It is preferred to use from 1 to 10% by weight silver halide in the layer, more preferably from 1.5 to 7%. The silver halide may be prepared in situ by conversion of a portion of silver soap by reaction with halide ions or it may be preformed and added during soap generation, or a combination of both methods may be used. The latter is preferred.

The silver halide may be sensitised to visible or infrared light by means of the appropriate dyes, which may be added to the mixture of silver halide and reducible silver salt, or when preformed silver halide is employed, spectral sensitisation may be carried out prior to mixing with the reducible silver salt, as described in U.S. Pat. No. 4,476,220. Spectral sensitising dyes for use in photothermographic media are well known in the art, and include cyanine dyes and merocyanine dyes as disclosed, for example in U.S. Pat. Nos. 3,761,279, 3,719,495, 3,877,943 and 4,835,096, and European Patent No. 127455. A preferred class of infrared sensitising dyes is disclosed in our copending British Patent Application No. 9305324.7, filed Mar. 16, 1993.

The reducible silver source may comprise any material which contains a reducible source of silver ions. Silver salts of organic and hetero-organic acids, particularly long chain fatty carboxylic acids (comprising from 10 to 30, preferably 15 to 25 carbon atoms), are preferred. Complexes of organic or inorganic silver salts in which the ligand has a gross stability constant for silver ion of between 4.0 and 10.0 are also useful.

Examples of suitable silver salts are disclosed in Research Disclosure Nos. 17029 and 29963 and include: salts of organic acids, e.g., gallic acid, oxalic acid behenic acid, stearic acid, palmitic acid, lauric acid and the like; silver carboxyalkylthiourea salts, e.g., 1-(3-carboxypropyl)thiourea, 1-(3-carboxypropyl)-3,3-dimethylthiourea and the like; complexes of silver with the polymeric reaction product of an aldehyde with a hydroxy-substituted aromatic carboxylic acid, e.g., aldehydes, such as formaldehyde, acetaldehyde and butyraldehyde, and hydroxy-substituted acids, such as salicylic acid, benzilic acid, 3,5-dihydroxybenzilic acid and 5,5-thiodisalicylic acid, silver salts or complexes of thiones, e.g., 3-(2-carboxyethyl)-4-hydroxymethyl-4-thiazoline-2-thione and 3-carboxymethyl-4-thiazoline-2-thione complexes or salts of silver with nitrogen acids selected from imidazole, pyrazole, urazole, 1,2,4-triazole and 1H-tetrazole, 3-amino-5-benzylthio-1,2,4-triazole and benzotriazole; silver salts of saccharin, 5-chlorosalicylaldoxime and the like; and silver salts of mercaptides.

The preferred silver source is silver behenate.

The reducible silver source generally comprises from 5 to 70%, preferably from 7 to 45% by weight of the imaging layer. The use of a second imaging layer in a two-layer construction does not affect the percentage of the silver source.

The reducing agent for silver ion may be any material, although organic materials are preferred which will reduce silver ion to metallic silver. Conventional photographic developers such as phenidone, hydroquinones and catechol are useful, but hindered phenol reducing agents are preferred. The reducing agent generally comprises from 1 to 10% by weight of the imaging layer, but in a two-layer construction, if the reducing agent is in the layer separate from that containing the reducible silver source, slightly higher proportions, e.g., from 2 to 15%, tend to be more desirable. Colour photothermographic materials, such as those disclosed in U.S. Pat. No. 4,460,681, are also contemplated in the practice of the present invention.

Examples of suitable reducing agents are disclosed in U.S. Pat. Nos. 3,770,448, 3,773,512 and 3,593,863 and Research Disclosure Nos. 17029 and 29963, and include aminohydroxycycloalkenone compounds, e.g., 2-hydroxypiperidino-2-cyclohexenone; esters of amino reductones as developing agent precursors, e.g., piperidino hexose reductone monoacetate; N-hydroxyurea derivatives, e.g., N-p-methylphenyl-N-hydroxyurea; hydrazones of aldehydes and ketones, e.g., anthracene aldehyde phenylhydrazone; phosphoramidophenols; phosphoramidoanilines; polyhydroxybenzenes, e.g., hydroquinone, t-butylhydroquinone, isopropylhydroquinone and (2,5-dihydroxyphenyl)methylsulfone; sulfhydroxamic acids, e.g., benzenesulfhydroxamic acid; sulfonamidoanilines, e.g., 4-(N-methanesulfonamido)aniline; 2-tetrazolylthiohydroquinones, e.g., 2-methyl-5-(1-phenyl-5-tetrazolylthio)hydroquinone; tetrahydroquinoxalones, e.g., 1,2,3,4,-tetrahydroquinoxaline; amidoxines; azines, e.g., a combination of aliphatic carboxylic acid aryl hydrazides and ascorbic acid; a combination of a polyhydroxybenzene and a hydroxylamine, a reductone and/or a hydrazine; hydroxamic acids; a combination of azines and sulfonamidophenols; α-cyanophenylacetic acid derivatives; a combination of a bis-β-naphthol and a 1,3-dihydroxybenzene derivative; 5-pyrazolones; sulfonamidophenol reducing agents; 2-phenylindane-1,3-dione and the like; chromans; 1,4-dihydropyridines, such as 2,6-dimethoxy-3,5-dicarbethoxy-1,4-dihydropyridine; bisphenols, e.g., bis(2-hydroxy-3-t-butyl-5-methylphenyl)methane, bis(6-hydroxy-m-toly) mesitol, 2,2-bis(4-hydroxy-3-methylphenyl)propane, 4,4-ethylidenebis(2-t-butyl-6-methylphenol, UV-sensitive ascorbic acid derivatives and 3-pyrazolidones.

The preferred developers are hindered phenols of the general formula:

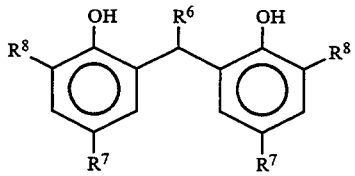

in which
R$^6$ represents hydrogen or an alkyl group generally comprising up to 15 carbon atoms, e.g., butyl, 2,4,4-trimethylpentyl etc, and
R$^7$ and R$^8$ represent H or alkyl groups of up to 5 carbon atoms, such as methyl, ethyl, t-butyl etc.

The presence of a toner (sometimes referred to as a "tone modifier") is not essential, but is highly preferred. Examples of suitable toners are disclosed in Research Disclosure No. 17029 and include: imides, e.g., phthalimide; cyclic imides, pyrazolin-5-ones and a quinazolinone, such as succinimide, 3-phenyl-2-pyrazolin-5-one, 1-phenylurazole, quinazoline and 2,4-thiazolidinedione; naphthalimides, e.g., N-hydroxy-1,8-naphthalimide; cobalt complexes, e.g., cobaltic hexammine trifluoroacetate, mercaptans, e.g., 3-mercapto-1,2,4-triazole; N-(aminomethyl)aryl dicarboximides, e.g., N-(dimethylaminomethyl)phthalimide; a combination of blocked pyrazoles, isothiuronium derivatives and certain photobleach agents, e.g., a combination of N,N'-hexamethylene bis(1-carbamoyl-3,5-dimethylpyrazole), 1,8-(3,6-dioxaoctane)bis(isothiuronium trifluoroacetate) and 2-(tribromomethylsulfonyl) benzothiazole); merocyanine dyes, such as 3-ethyl-5-[(3-ethyl-2-benzothiazolinylidene)-1-methylethylidene]-2-thio-2,4-oxazolidinedione; phthalazinone, phthalazinone derivatives or metal salts of these derivatives, such as 4-(1-naphthyl)phthalazinone, 6-chlorophthalazinone, 5,7-dimethoxyphthalazinone and 2,3-dihydro-1,4-phthalazinedione; a combination of phthalazinone and a sulfinic acid derivative, e.g., 6-chlorophthalazinone plus sodium benzene sulfinate or 8-methylphthalazinone plus sodium p-tolysulfinate; a combination of phthalazinone plus phthalic acid; a combination of phthalazine including an adduct of phthalazine and maleic anhydride) and at least one compound selected from phthalic acid, a 2,3-naphthalene dicarboxylic acid or an o-phenylene acid derivative and anhydrides thereof, e.g., phthalic acid, 4-methylphthalic acid, 4-nitrophthalic acid and tetrachlorophthalic anhydride; quinazolinediones, benzoxazine and naphthoxazine derivatives; benzoxazine-2,4-diones, e.g., 1,3-benzoxazine-2,4-dione; pyrimidines and asym-triazines, e.g., 2,4-dihydroxypyrimidine, and tetraazapentalene derivatives, e.g., 3,6-dimercapto-1,4-diphenyl-1H,4H -2,3a,5,6a-tetraazapentalene.

Preferred toners are phthalazinone, phthalazine and 4-methylphthalic acid, either alone or in combination with other compounds.

The toner, when present, is generally included in an amount of from 0.2 to 12%, preferably 0.2 to 5% by weight of the imaging layer.

The photothermographic chemistry is typically applied to the support in a binder. A wide range of binders may be employed in the imaging layer(s), including both natural and synthetic resins. Copolymers and terpolymers are of course included. Suitable binders are transparent or translucent, are generally colourless and include natural polymers, synthetic resins, polymers and copolymers and other film forming media such as: gelatin; gum arabic; poly(vinyl alcohol); cellulose esters, such as hydroxyethyl cellulose, cellulose acetate, cellulose acetate butyrate; poly(vinyl pyrrolidone); casein; starch; poly(acrylic acid), poly(methylmethacrylic acid), poly(methacrylic acid); poly(vinyl chloride); copoly(styrene-maleic anhydride), copoly(styrene-acrylonitrile), copoly(styrene-butadiene); polyacrylonitrile; polyvinyl acetals, such as, poly(vinyl formal) and poly(vinyl butyral); polyesters; polyurethanes; phenoxy resins; poly(vinylidene chloride); polyepoxides; polycarbonates; poly(vinyl acetate); polyolefins, such as poly(ethylene) and poly(propylene), and polyamides. Poly(vinyl acetals), such as poly(vinyl butyral) and poly(vinyl formal), and vinyl copolymers, such as poly(vinyl acetate-chloride) are particularly desirable. The binders are generally used in an amount ranging from 20 to 75% by weight, preferably from 30 to 55% by weight of the silver halide containing layer. The binders may be coated from aqueous or organic solvents or an emulsion.

The photothermographic elements of the invention are prepared by simply coating a suitable support or substrate with the one or more imaging layers containing the photothermographic chemistry and, optionally, a oxygen-barrier overlayer. Suitable barrier layers are well known in the art. Each layer is generally coated from a suitable solvent using techniques known in the art. Exemplary supports include materials, such as paper, polyethylene-coated paper, polypropylene-coated paper, parchment, cloth and the like; sheets and foils of metals, such as aluminium, copper, magnesium and zinc; glass and glass coated with metals such as chromium alloys, steel, silver, gold and platinum; synthetic polymeric materials, such as poly(alkyl methacrylates), e.g., poly(methyl methacrylate), polyesters, e.g., poly(ethylene terephthalate) and poly(ethylene naphthalate), poly(vinyl acetals), polyamides, e.g., nylon, cellulose esters, e.g., cellulose nitrate, cellulose acetate, cellulose acetate propionate, cellulose acetate butyrate, and the like.

Various other adjuvants may be added to the photothermographic medium. For example, accelerators, acutance dyes, sensitizers, stabilizers, plasticizers, surfactants, lubricants, coating aids, antifoggants, leuco dyes, chelating agents, binder crosslinking agents, UV-absorbers and various other well-known additives may be usefully incorporated in the medium. The use of acutance dyes matched to the spectral emission of the exposure source is particularly desirable. It is not essential for the photothermographic elements of the invention to comprise a separate support since each binder layer, together with the photothermographic chemistry may be cast to form a self-supporting film.

The supports can be sub-coated with known subbing materials such as: copolymers and terpolymers of vinylidene chloride; and acrylic monomers, such as acrylonitrile and methyl acrylate; unsaturated dicarboxylic acids, such as itaconic or acrylic acid; carboxymethyl cellulose; polyacrylamide, and similar polymeric materials.

The support can also carry a filter or antihalation layer, such as one comprising a dyed polymer layer, which absorbs the exposing radiation after it passes through the radiation-sensitive layer and eliminates unwanted reflection from the support.

The invention will now be illustrated by the following Examples.

EXAMPLE 1

Preparation of 2-tribromomethylsulphonyl-5-methyl-1,3,4-thiadiazole (Compound A)

(i) preparation of 2-carboxymethylthio-5-methyl-1,3,4-thiadiazole.

Chloroacetic acid (21 g) was added to a slurry of sodium hydrogen carbonate (35.3 g) in ethanol:water (1:1 480 ml). 2-mercapto-5-methyl-1,3,4-thiadiazole (26.4 g) was added slowly and the mixture refluxed for 6 hours. The volume was reduced to about 200 ml and cooled to room temperature. Hydrochloric acid (12N, 15.5 ml) was added and the resulting white precipitate was collected by filtration, washed with water and dried in vacuo. Yield 30.3 g (84%).

(ii) Preparation of 2-tribromomethylsulphonyl-5-methyl-1,3,4,-thiadiazole (compound A).

Sodium hydroxide (91.8 g) was dissolved in water (2.5l) and cooled to 2° C., Bromine (57.6 ml) was added slowly keeping the temperature at 2° C., and the mixture was stirred until all the bromine was consumed. The carboxymethylthiothiadizole (26.6 g) from (i) above was dissolved in water (310 ml) together with sodium hydrogen carbonate (12.8 g). This solution was added slowly to the bromine solution keeping the temperature below 5° C. The mixture was allowed to warm to room temperature overnight during which time the product crystallised out. The product was collected by filtration and recrystallised from ethanol. Yield 11.3 g (19.4%) melting point: 169°–173° C.

EXAMPLE 2

Skin Sensitivity Tests

Compound A of Example 1 was compared with two compounds within the scope of U.S. Pat. No. 3,874,946, which discloses image stabilisers for photothermographic materials.

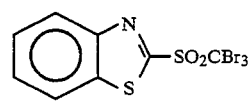

Compound B

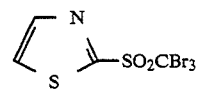

Compound C

Procedure for skin sensitivity tests (guinea-pig)

The guinea pig maximization test protocol as described by B. Magnusson and A. Kligman in Allergic Contact Dermatitis in the Guinea Pig, C. C. Thomas, ed. pp 113–117 (1970) was used. The compounds were screened for irritation. None of the compounds caused skin irritation to guinea pigs after application as a 25% w/w suspension in petrolatum (mineral oil) for 24 hours.

A sensitization test was conducted. For each compound, ten male guinea pigs were assigned to the test group and four male guinea pigs were assigned to the naive control group. On day 1, animals in the test group received duplicate 0.05 ml intradermal injections of a 1:1 ratio of Freund's Complete Adjuvant in sterile water, a 5% w/v suspension of the test compound in mineral oil and a 5% w/v suspension of the test compound in Freund's Complete Adjuvant and sterile water on the shoulder area. Six days later, animals in the test group were pretreated with sodium lauryl sulphate applied topically at the injection sites. On clay eight, a 25% w/w mixture of the test compound in petrolatum was applied over the injection sites of the animals and occluded for 48 hours. The naive control animals were not treated during the induction phase.

Two weeks after the topical application, all animals received a challenge dose. A 25% w/w mixture of the test compound in petrolatum was applied to the right flank of the test and naive control (previously untreated) animals. All sites were occluded for 24 hours and then wiped clean. Test sites were examined for erythema reactions at 24 and 48 hours after patch removal. In no case was reaction seen in the naive control animals.

Compound A 0 out of 10 animals showed reactions.

Compound B 10 out of 10 animals showed moderate to intense dermal reactions (extreme sensitiser).

Compound C 10 out of 10 animals showed mild to intense dermal reactions (extreme sensitiser).

EXAMPLE 3

Photographic properties

A series of black and white photothermographic elements were prepared:

Silver soap underlayer

The following ingredients were added to a preformed full soap homogenate (100 g) in which the silver halide was a 50:50 mixture of silver iodobromide (0.05 μm grain size) and silver iodobromide (0.07 μm) with stirring as indicated:

Methyl ethyl ketone (50 ml) stirring for 5 minutes;
BUTVAR B-76 (33 g) stirring for 25 minutes;
Pyridinium hydrobromide perbromide (3×0.06 g) in methanol (5 ml) stirring for 2 hours and
calcium bromide (10% solution in methanol; 1-3 ml) stirring for 30 minutes.

All operations were carried out in a minus blue light environment, ordinarily in a Red 1A Safelight area, and at a temperature of 7° C. (unless otherwise indicated). The resulting mixture was stored overnight in a sealed container at 7° C. before warming to 21° C. and continuing by adding the following:

NONOX 1,1-Bis(2-hydroxy-3,5-dimethylphenyl)-3,5,5-trimethylhexane (7 g), 2-(4-chlorobenzoyl)-benzoic acid (12% solution in methanol; 10 ml) stirring for 30 minutes;
2-mercaptobenzimidazole (0.5% solution in methanol; 6.4 ml) stirring for 15 minutes,
Sensitising Dye, stirring for 15 minutes.

Topcoat

The following ingredients were stirred or placed in an ultrasonic bath until a clear solution was obtained. The resulting solution was allowed to stand for 1 hour at 21° C. before use:

| | |
|---|---|
| acetone | 140 ml |
| methylethylketone | 67 ml |
| methanol | 27.5 ml |
| cellulose acetate | 9 g |
| phthalazine | 1 g |
| 4-methylphthalic acid | 0.72 g |
| tetrachlorophthalic acid | 0.22 g |
| tetrachlorophthalic anhydride | 0.5 g |
| Compound A (invention) or Compound B (comparison) | 0.2/0.4/0.8/1.2 g |

Once dry the materials were imaged by conventional means. Comparative results for Development latitude, film aging (anti-foggant) and print stability are reported in the following Tables.

TABLE 1

| | Measurement of Dmin | | | |
|---|---|---|---|---|
| Development time/temp | 3 s/ 290° F. | 6 s/ 275° F. | 6 s/ 260° F. | 12 s/245° F. |
| Compound A 0.2 g | 0.14 | 0.14 | 0.22 | 0.12 |
| Compound B 0.2 g | 0.19 | 0.22 | 0.4 | 0.19 |
| Compound A 0.4 g | 0.13 | 0.13 | 0.18 | 0.11 |
| Compound B 0.4 g | 0.15 | 0.19 | 0.23 | 0.16 |
| Compound A 0.8 g | 0.11 | 0.11 | 0.14 | 0.11 |
| Compound B 0.8 g | 0.13 | 0.13 | 0.16 | 0.12 |
| Compound A 1.2 g | 0.10 | 0.11 | 0.13 | 0.10 |
| Compound B 1.2 g | 0.11 | 0.12 | 0.16 | 0.13 |

TABLE 2

| | Measurement of Dmax | | | |
|---|---|---|---|---|
| Development time/temp | 3 s/ 290° F. | 6 s/ 275° F. | 6 s/ 260° F. | 12 s/245° F. |
| Compound A 0.2 g | 1.60 | 1.63 | 1.63 | 1.63 |
| Compound B 0.2 g | 1.56 | 1.59 | 1.60 | 1.59 |
| Compound A 0.4 g | 1.60 | 1.63 | 1.63 | 1.63 |
| Compound B 0.4 g | 1.58 | 1.62 | 1.63 | 1.60 |
| Compound A 0.8 g | 1.61 | 1.63 | 1.61 | 1.64 |
| Compound B 0.8 g | 1.56 | 1.60 | 1.59 | 1.59 |
| Compound A 1.2 g | 1.60 | 1.62 | 1.62 | 1.63 |
| Compound B 1.2 g | 1.56 | 1.57 | 1.59 | 1.59 |

TABLE 3

| Anti-foggant properties - Dmin after aging unexposed film 120° F. at 50% RH Developed 6 sec at 250° F. | | | | | |
|---|---|---|---|---|---|
| Days aging | 0 | 7 | 14 | 21 | 28 |
| Compound A 0.2 g | 0.14 | 0.13 | 0.14 | 0.19 | 0.37 |
| Compound B 0.2 g | 0.22 | 0.16 | 0.15 | 0.14 | 0.27 |
| Compound A 0.4 g | 0.13 | 0.12 | 0.10 | 0.12 | 0.20 |
| Compound B 0.4 g | 0.18 | 0.13 | 0.12 | 0.12 | 0.11 |
| Compound A 0.8 g | 0.11 | 0.10 | 0.10 | 0.09 | 0.11 |
| Compound B 0.8 g | 0.14 | 0.11 | 0.10 | 0.11 | 0.09 |
| Compound A 1.2 g | 0.11 | 0.09 | 0.09 | 0.09 | 0.09 |
| Compound B 1.2 g | 0.12 | 0.11 | 0.10 | 0.09 | 0.09 |

TABLE 4

| Anti-foggant properties Dmax after aging unexposed film 120° F. at 50% RH Developed 6 sec at 250° F. | | | | | |
|---|---|---|---|---|---|
| Days aging | 0 | 7 | 14 | 21 | 28 |
| Compound A 0.2 g | 1.63 | 1.60 | 1.57 | 1.57 | 1.55 |
| Compound B 0.2 g | 1.59 | 1.59 | 1.56 | 1.55 | 1.57 |
| Compound A 0.4 g | 1.63 | 1.59 | 1.56 | 1.56 | 1.54 |
| Compound B 0.4 g | 1.61 | 1.58 | 1.55 | 1.56 | 1.54 |
| Compound A 0.8 g | 1.63 | 1.58 | 1.54 | 1.54 | 1.53 |
| Compound B 0.8 g | 1.60 | 1.57 | 1.53 | 1.54 | 1.52 |
| Compound A 1.2 g | 1.63 | 1.57 | 1.54 | 1.52 | 1.48 |
| Compound B 1.2 g | 1.57 | 1.57 | 1.53 | 1.52 | 1.51 |

TABLE 5

| Print stabilisation properties - Dmin after exposing processed film on the table top at 55 fcs, Developed 6 sec at 250° F. | | | | |
|---|---|---|---|---|
| Days aging | 0 | 21 | 57 | 150 |
| Compound A 0.2 g | 0.14 | 0.15 | 0.16 | 0.18 |
| Compound B 0.2 g | 0.22 | 0.24 | 0.24 | 0.27 |
| Compound A 0.4 g | 0.13 | 0.14 | 0.14 | 0.16 |
| Compound B 0.4 g | 0.18 | 0.19 | 0.20 | 0.21 |
| Compound A 0.8 g | 0.11 | 0.12 | 0.12 | 0.14 |
| Compound B 0.8 g | 0.14 | 0.15 | 0.16 | 0.16 |
| Compound A 1.2 g | 0.11 | 0.12 | 0.12 | 0.15 |
| Compound B 1.2 g | 0.12 | 0.15 | 0.16 | 0.16 |

Compound A of the invention exhibit improved photographic properties compared with compound B. Although exemplified in monochromatic photothermographic materials, the use of the compounds of this invention can also be applied to colour photothermographic materials.

We claim:

1. A photothermographic material comprising photographic silver halide, a reducible silver source, a reducing agent for silver ion, and a binder, and, as an antifoggant and/or image stabilizer, a compound of the formula:

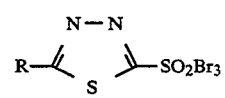

wherein:
R is a member selected from the group consisting of a hydrogen atom, an alkyl group, an aryl group and a heterocyclic group.

2. A photothermographic material according to claim 1 wherein R is a member selected from the group consisting of an alkyl group of 1 to 5 carbon atoms, an aryl group containing up to 10 skeletal atoms in one or more rings and a heterocyclic group containing up to 10 skeletal atoms in one or more rings.

3. A photothermographic material according to claim 1 wherein said compound of formula (I) is present in an amount from $1 \times 10^{-3}$ to $1 \times 10^{-1}$ moles per mole of silver halide.

4. A photothermographic material according to claim 1 which additionally comprises, as a speed enhancing agent, a heterocyclic ring compound in which a nitrogen atom of the ring is electrically balanced by hydrobromic acid and is associated with a pair of bromine atoms.

5. A photothermographic material according to claim 4 wherein the hydrobromic acid salt comprises a compound having a central nucleus which is a member selected from the group consisting of:

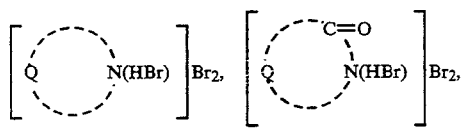

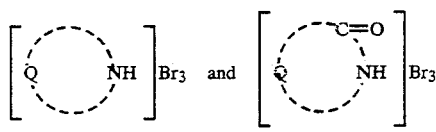

wherein;

Q comprises the atoms necessary to complete a 5, 6, or 7-membered heterocyclic ring nucleus.

6. A photothermographic emulsion according to claim 5 wherein Q completes a nucleus which is a member selected from the group consisting of pyridine, pyrrolidone and pyrrolidinone ring nucleus.

7. A photothermographic material according to claim 6 wherein the hydrobromic acid salt comprises a compound having a central nucleus which is a member selected from the group consisting of:

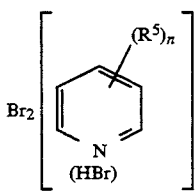

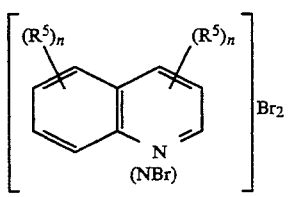

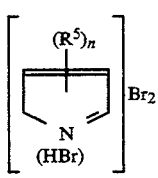

-continued

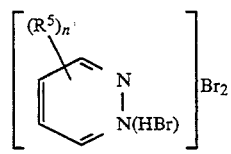

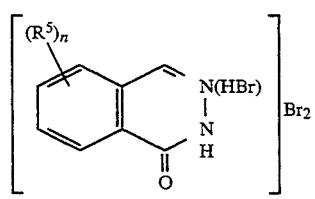

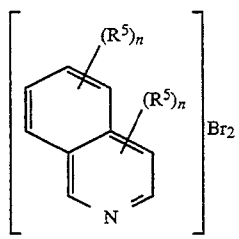

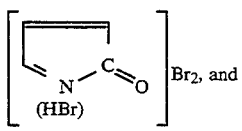

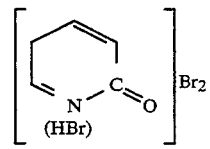

wherein;

n is 0 (zero) or has integral values of from 1 to 4, and each $R^5$ is a member selected from the group consisting of a hydrogen atom, an alkyl group, an aryl group and a heterocyclic group.

8. A photothermographic material according to claim 4 wherein the hydrobromic acid salt is pyridinium hydrobromide perbromide.

9. A photothermographic material according to claim 1 which comprises, as reducible silver source, a member selected from the group consisting of a silver salt, a silver complex of an organic acid and a silver complex of a hetero-organic acid.

10. A photothermographic material according to claim 9 wherein the reducible silver source is the silver salt of behenic acid.

11. A photothermographic material according to claim 9 comprising, as a reducing agent for silver ion, a member selected from the group consisting of a phenidone, hydroquinone, catehol and a hindered phenol.

12. A photothermographic element according to claim 11 wherein the hindered phenol has a nucleus of the general formula:

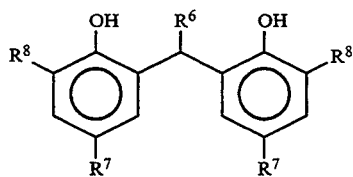

wherein;

$R^6$ is a member selected from the group consisting of hydrogen and an alkyl group comprising up to 15 carbon atoms and $R^7$ and $R^8$ are independently members selected from the group consisting of hydrogen and alkyl groups of up to 5 carbon atoms.

13. A photothermographic element according to claim 11 wherein the reducing agent is used in combination with a toner.

14. A photothermographic element according to claim 13 wherein the toner is a member selected from the group consisting of phthalazinone, phthalazine, phthalic acid and combinations thereof.

* * * * *

UNITED STATES PATENT AND TRADEMARK OFFICE
CERTIFICATE OF CORRECTION

PATENT NO. : 5,374,514
DATED : December 20, 1994
INVENTOR(S) : Kirk et al.

It is certified that error appears in the above-indentified patent and that said Letters Patent is hereby corrected as shown below:

Column 10, line 40, delete "clay" and insert --day--.

Signed and Sealed this

Second Day of May, 1995

Attest:

BRUCE LEHMAN

*Attesting Officer*     *Commissioner of Patents and Trademarks*